United States Patent [19]
Taylor et al.

[11] Patent Number: 5,382,660
[45] Date of Patent: Jan. 17, 1995

[54] TCPG GENE OF VIBRIO CHOLERAE

[75] Inventors: Ronald K. Taylor, Cordova; Joel A. Peek, Memphis, both of Tenn.

[73] Assignee: The University of Tennessee Research Corporation, Knoxville, Tenn.

[21] Appl. No.: 782,113

[22] Filed: Oct. 25, 1991

[51] Int. Cl.⁶ ................... C12N 15/31; C12N 15/52
[52] U.S. Cl. ............................. 536/23.2; 536/23.1; 536/23.7
[58] Field of Search ............... 536/27, 23.1, 23.2, 536/23.7; 435/69.1, 71.1, 320.1

[56] References Cited

PUBLICATIONS

C. B. Anfinsen, et al., "The Kinetics of Formation of Nature Ribonuclease during Oxidation of the Reduced Polypeptide Chain", *Proc. Natl. Acad. Sci. USA*, vol. 47(9), pp. 1209–1314 (1961).

J. J. Mekalanos, et al., "Simple Method for Purifying Choleragenoid, The Natural Toxoid of *Vibrio cholerae*", *Infect. immun.*, vol. 6(3), pp. 789–795 (1977).

D. M. Gill, "Mechanism of Action of Cholera Toxin", in *Advances in Cyclic Nucleotide Research*, ed. P. Greegard, et al., Raven Press, New York, pp. 85–118 (1977).

A. Holmgren, "Thioredoxin Catalyzes The Reduction of Insulin Disulfides by Dithiothreitol and Dihydrolipoamide", *J. Biol. Chem.*, vol. 254, pp. 85–118 (1977).

M. Meng, et al., "Purification, Characterization, and Amino Acid Sequence of Thioredoxin from *Corynebacterium nephridii*", *J. Biol. Chem.*, vol. 256(17), pp. 9174–8182 (1981).

I. G. Haas, et al., "Immunoglobulin Heavy Chain Binding Protein", *Nature*, vol. 306, pp. 387–389 (1983).

R. B. Freedman, "Native Disulphide Band Formation in Protein, Biosythesis; Evidence for the Role of Protein Disulphide Isomerase", *Trends Biochem. Sci.*, vol. 9, pp. 438–441 (1984).

J. C. Edman, et al., "Sequence of Protein Disulphide Isomerase and Implications of Its Relationship to Thioredoxin", *Nature*, vol. 317, pp. 267–270 (1985).

R. K. Taylor, et al., "Use of *phoA* Gene Fusions to Identify a Pilus Colonization Factor Coordinately Regulated With Cholera Toxin", *Proc. Natl. Acad. Sci. USA*, vol. 84, pp. 2833–2837 (1987).

R. Jaenicke, "Folding and Association of Proteins", *Prog. Biophys. Mol. Bio.*, vol. 49, pp. 117–237 (1987).

K. M. Peterson, et al., Characterizatin of the *Vibrio cholerae* ToxR Regulon: Identification of Novel Genes Involved in Intestinal Colonization:, *Infect. Immun.*, vol. 56(11), pp. 2822–2829 (1988).

R. B. Breedman, et al., "Role of Protein Disulphide–Isomerase in the Expression of Native Proteins", *Biochem. Soc. Symp.*, vol. 55, pp. 167–192 (1989).

D. Sun, et al., "Localization of Protective Epitopes Within the Pilin Subunit of the *Vibrio cholerae* Toxin–Coregulated Pilus", *Infect. Immun.*, vol. 59(2), pp. 114–118 (1991).

*Primary Examiner*—Richard A. Schwartz
*Assistant Examiner*—Robert A. Hodges
*Attorney, Agent, or Firm*—Weiser Associates

[57] ABSTRACT

A method for increasing the yield of recombinant non-bacterial or bacterial gene products from bacteria comprising inserting a non-bacterial or bacterial gene into the genetic material of the bacteria whereby the inserted gene is co-expressed with a desired recombinant non-bacterial or bacterial gene product and aids the arrangement of the gene product into the proper final conformation. The non-bacterial or bacterial gene for insertion into the genetic material is also disclosed.

1 Claim, No Drawings

TCPG GENE OF VIBRIO CHOLERAE

The present invention was developed, in part, with funds from the United States Public Health Service (Grant AI-25096) and the National Institutes of Health (Grant AI-07238). The United States government has certain rights in the present invention.

The present invention relates to the production of recombinant non-bacterial or bacterial products from bacteria. In particular, the present invention relates to methods for increasing the yield of the recombinant products.

In recent years, a major triumph of the biotechnology industry has been the production of non-bacterial or bacterial proteins from bacteria. Human insulin is currently being produced from bacteria such as *E. coli*, and other important genetic products, such as interferon, human growth hormone, and other proteins, are also being produced in a scale heretofore unattainable by other methods. In general, the process involves the insertion of genetic material which encodes the appropriate non-bacterial or bacterial protein into the genetic material of a bacterium. The bacterial genetic material may comprise either the bacterial genome itself or plasmids existing in the body of the bacterium. The non-bacterial or bacterial genes are placed under the control of an operon which is operable due to a chemical trigger supplied from the outside. For example, the addition of a particular sugar to a bacterial strain could induce the production of human insulin in *E. coli*. The operon triggers the production of proteins from the genetic material located in the bacterium.

As the proteins are produced they have a tendency to form oxidized Cys-S-S-Cys bonds between cystein amino acids in the protein. These bonds have a tendency to cause the protein to misfold as the protein is produced. This misfolding yields a non-operative protein which eventually forms into an inclusion body within the bacterium.

Currently, in the industrial application of the bacterial production of proteins, the bacteria are allowed to produce the proteins despite the misfolding and formation of inclusion bodies. After a sufficient amount of protein has been produced, the inclusion bodies are separated from the bacteria and treated with thioredoxin which helps the proteins unfold and refold into the appropriate conformation. Unfortunately, this process yields only about 30% of the total proteins produced. Therefore, a large majority of the proteins which were initially produced are non-recoverable.

The amount of time and effort required to remove the inclusion bodies and treat them with thioredoxin increases the cost of the recovered protein. In addition, the loss of 70% of the protein further increases the final cost of the product. Accordingly, there is a need for circumventing the isolation of inclusion bodies and treatment with thioredoxin in attempting to recover the protein product.

It is an object of the present invention to provide an improved method for producing a protein employing a bacteria host. It is another object to provide a method for producing a protein employing a bacteria host in which the protein product substantially will not misfold upon expression in the bacterial genetic material.

It is another object of the present invention to provide a gene sequence for insertion into bacterial genetic material which may be coexpressed with non-bacterial or bacterial genetic material of interest.

The present invention provides an improvement in the method of production of a non-bacterial or bacterial protein from bacterial genetic material of the type wherein a first nucleic acid sequence is inserted into the genetic material, the sequence is placed under the control of an operon which is inducible, the operon is induced, and the protein is produced. The improvement comprises inserting into the bacterial genetic material a second nucleic acid sequence under the control of the operon whereby the second nucleic acid sequence is coexpressed with the first nucleic acid sequence to produce from the expression of the second nucleic acid sequence a second protein that is operable to aid the first non-bacterial or bacterial protein enfolding to an operable conformation.

In a preferred embodiment of the present invention the second nucleic acid sequence is the TcpG gene from the *Vibrio cholerae* bacterium. Further, the TcpG gene has the sequence SEQ ID NO:1:

```
ATAAATCCAATGGAGAAAGTCATGAAAAAGCTGTTTGCACTGGTTGCAACT
CTGATGTTAAGCGTGTCAGCCTATGCGGCTCAATTTAAAGAAGGTGAACAC
TACCAAGTGTTAAAAACACCCGCCTCTTCTTCACCAGTCGTCAGTGAGTTT
TTCTCATTCTACTGCCCGCACTGTAACACTTTCGAACCCATTATTGCTCAG
TTGAAGCAGCAGTTGCCTGAAGGCGCGAAATTCCAGAAAAACCACGTCTCT
TTCATGGGTGGTAACATGGGTCAAGCGATGAGCAAAGCGTACGCAACCATG
ATTGCTCTGGAAGTGGAAGATAAAATGGTACCTGTGATGTTTAACCGCATC
CACACTCTGCGTAAACCACCGAAAGATGAACAAGAGCTGCGCCAAATCTTC
CTAGATGAAGGAATTGATGCGGCGAAATTTGATGCGGCTTACAACGGCTTT
GCCGTGGATTCTATGGTGCGCCGTTTCGATAAACAGTTCCAAGATAGCGGC
CTAACCGGTGTACCTGCCGTTGTTGTTAACAACCGTTATTTGGTACAAGGT
CAGTCCGTCAAATCCCTCGACGAATATTTTGACCTAGTGAACTACCTGCTG
ACGCTGAAGTAA
```

In accordance with the present invention there also is provided a nucleic acid sequence suitable for insertion into genetic material of a bacterium and which may be coexpressed with a further nucleic acid sequence to produce a protein from the first nucleic acid sequence which is the product of the second nucleic acid sequence enfolding into an operable conformation. In a preferred embodiment, the sequence comprises the TcpG gene from the *Vibrio cholerae* bacterium. Further, the TcpG gene comprises the sequence SEQ ID NO:1:

```
ATAAATCCAATGGAGAAAGTCATGAAAAAGCTGTTTGCACTGGTTGCAACT
CTGATGTTAAGCGTGTCAGCCTATGCGGCTCAATTTAAAGAAGGTGAACAC
TACCAAGTGTTAAAAACACCCGCCTCTTCTTCACCAGTCGTCAGTGAGTTT
TTCTCATTCTACTGCCCGCACTGTAACACTTTCGAACCCATTATTGCTCAG
```

-continued
```
TTGAAGCAGCAGTTGCCTGAAGGCGCGAAATTCCAGAAAAACCACGTCTCT
TTCATGGGTGGTAACATGGGTCAAGCGATGAGCAAAGCGTACGCAACCATG
ATTGCTCTGGAAGTGGAAGATAAAATGGTACCTGTGATGTTTAACCGCATC
CACACTCTGCGTAAACCACCGAAAGATGAACAAGAGCTGCGCCAAATCTTC
CTAGATGAAGGAATTGATGCGGCGAAATTTGATGCGGCTTACAACGGCTTT
GCCGTGGATTCTATGGTGCGCCGTTTCGATAAACAGTTCCAAGATAGCGGC
CTAACCGGTGTACCTGCCGTTGTTGTTAACAACCGTTATTTGGTACAAGGT
CAGTCCGTCAAATCCCTCGACGAATATTTTGACCTAGTGAACTACCTGCTG
ACGCTGAAGTAA
```

The non-bacterial or bacterial gene sequence inserted into the bacterial genetic material for increasing the yield of recombinant non-bacterial or bacterial products may be placed under the control of a single operon. Optionally the control may be placed under more than one operon in the bacterial gene. Employing multiple operon control has been found to enhance production of the protein which aids in the folding of the desired protein product into the proper conformation will be produced. Increased production of the protein to aid folding does not affect the yield of the desired protein product.

The idea that protein conformation is dictated solely by amino acid sequence has long been considered the fundamental principal behind protein folding. This model was initially reinforced by in vitro refolding studies of small proteins following denaturation. This type of global refolding system appears to be analogous to what occurs in the cytoplasm of cells, but does not take into account the multiple physicochemical environments encountered by translocated polypeptides. This matter becomes further complicated when large polypeptides or ones containing intrachain disulfide bonds are assayed. In this case, the yield of mature refolded molecules is usually significantly reduced, resulting in improperly folded nonfunctional molecules and nonspecific aggregates of unfolded chains.

The means by which secreted polypeptides mature to their functional conformation are certainly more complex than those original artificial global folding systems which expose all portions of a polypeptide chain to the same physicochemical environmental simultaneously. For example, as a polypeptide is translocated across a lipid membrane, it is being exposed to at least two different physicochemical environments, each with its own folding parameters. With nothing to prevent folding as a polypeptide emerges on the distal side of a membrane, the emerging distal portions often form nonspecific aggregates, assume an improper conformation due to the lack of information containing cytoplasmic residues, or be nonfunctional because of a prohibited modification event caused by a prematurely assumed tertiary structure. Then it is likely that the successful folding of some translocated polypeptides may require antifolding chaperons or isomerases on the distal side of the membrane.

Without being bound by theory, it is believed that a class of bacterial periplasmic proteins exists. These proteins are believed to be exemplified by TcpG. It is believed that this protein participates during the functional maturation of secreted and multimeric proteins to relieve the problems encountered by translocated polypeptides. Thus, it is believed that TcpG acts to locate and guide portions of polypeptide chains into a state whereby complex surfaces can form. These surfaces might otherwise be energetically unfavorable and would rarely form under physiological conditions.

Proteins with cysteine amino acids (nearly all proteins) get oxidized as they leave the cytoplasm to go to the periplasm or father out of a bacterial cell. This results in a thiol-SH on the cysteine (Cys) being converted to a disulfide by linking to another Cys. Thus two Cys-SH's go to Cys-S-S-Cys. This is required for the proper final conformation of these proteins to be achieved. The present inventors have found that this bond formation does not result in appropriate protein conformation unless it is catalyzed by a "chaperone" type of enzyme, in this case TcpG. The enzyme binds a variety of proteins and helps them fold, and in so doing, reducing and allowing the disulfide bonds to reform.

In order to provide a better understanding of the present invention, the following procedures are given by way of illustration and not by way of limitation. The procedure demonstrates the isolation and identification of the TcpG gene sequence and the TcpG protein produced from the sequence. In addition, the procedure demonstrates the requirement of the TcpG protein for providing the proper conformation for various toxin proteins from *V. cholerae*.

EXAMPLE

A. Cloning the TcpG-PhoA fusion. Chromosomal DNA isolated from *Vibrio cholerae* strain KP8-96 was digested with BamHI, ligated into similarly digested pBR322 and transformed into *E. coli* strain MC1061. Strain KP8-96 carries a mutation of TcpG which prevents the proper expression of the gene. Transformants were selected on agar containing kanamycin (45 μg/ml), ampicillin (100 μg/ml) and the alkaline phosphatase-chromogenic substrate XP (5-bromo-4-chloro-3-indolyl phosphate, 40 μg/ml). Two antibiotic resistant blue colonies resulted. Both recombinant plasmids were shown by restriction analysis to contain a 6.7 kb BamHI fusion fragment, of which 1.7 kb was Vibrio DNA with the remainder being from TnphoA. The plasmid used throughout this study is referred to as p8-96.1.

B. Make of DNA sequence determination. The BamHI fragment of p8-96.1 was subcloned into the BamHI restriction site of M13mp18 and transformed into JM103 derivative strain JF626. Additional subclones generated in both mp18 and mp19 were used to determine the DNA sequence from both strands by the dideoxynucleotide chain termination method utilizing the universal lac, phoA and additional 20 bp synthetically generated primers. Sequence analyses were performed utilizing Wisconsin Genetics Computer Group Algorithms.

C. Antibodies directed against TcpG. Kyte and Doolittle analysis indicated a strong hydrophilic peak corresponding to residues 121-144 of the predicted TcpG amino acid sequence. A 23 amino acid peptide, peptide #1, corresponding to this region was synthesized on an Applied Biosystems peptide synthesizer. A carboxy-terminal cysteine added to the C-terminus of the peptide was used to facilitate KLH coupling. The KLH coupled peptide #1 was resuspended in 0.15M PBS and emulsified at a 1:1 ratio with Freund's complete adjuvant or the Ribi's adjuvant according to reconstitution instructions provided by Immunochem. Research Inc. Rabbits were bled for pre-immune sera and then immunized with 150–200 μg of the antigen. Following a routine immunization protocol the rabbits were bled and then boosted with 75–150 μg of antigen solubilized in PBS (Freud's Rab.) or Ribi's adjuvant. Either antiserum was used to detect TcpG by Western immunoblot and both are collectively referred to as "anti-TcpG antiserum".

D. Purification of TcpG. Aerated cultures of 0395 were grown in LBpH6.5 at 30° C. (TCP expressing conditions) to an optical density of 1.7–1.9 at 600 nm. These cells were chilled on ice and pelleted at 10,000×G for 10 minutes. Cells were then resuspended in cold 0.15M PBS with 20 fold concentration. A stock solution of 10 mg/ml polymyxin B sulfate in 0.15M PBS was added to the cells to a final concentration of 2 mg/ml. This mixture was gently stirred in an ice bath for 10–12 minutes. Spheroplasts and whole cells were removed by centrifugation at 10,000×G for 10 minutes. The supernatant was then dialyzed against 10 mM Tris-HCl, 1 mM EDTA pH 6.8 overnight at 4° C. and concentrated about 4 fold by ultrafiltration using an Amicon PM10 membrane at 50 lb/in$^2$ of $N_2$ at 4° C. The retenate was applied to a column of DEAE (DE52) cellulose (2.6×15 cm) which had been equilibrated with 10 mM Tris-HCl, 1 mM EDTA pH6.8 at 4° C. These ionic conditions were such that TcpG eluted with the flow through of the DEAE column. Flow through fractions were analyzed by Western blot and TcpG containing fractions pooled and concentrated as above. The concentrated TcpG fractions were applied to a column of G-100 Sephadex (1.6×96 cm) which had been equilibrated with 50 mM Tris-HCl mM EDTA pH6.8. Fractions of 1 ml each were collected at a flow rate of 12 ml/hr. TcpG containing fractions were identified by Western blot and by insulin assay.

E. Insulin assay. The catalyzed reduction of insulin in the presence of DTT was measured turbidmetrically at 600 nm. Reaction mixtures contained 500 μl of 1 mg/ml insulin in 0.1M potassium phosphate buffer pH 7.0, 2 mM EDTA, and 3–20 μg of sample. Water was added to a final volume of 61 ml. The reaction was started with the addition of 1–5 μl of 100 mM DTT. Measurements were taken at 60 second intervals for 60–80 minutes. Measurements were again taken at approximately 24 hours to assure that additional reducing potential was not contained in any of the samples. Slopes of the DTT control and the reaction samples were determined and activities calculated. The assay parameters were first worked out utilizing lyophilized *E. coli* thioredoxin (Sigma) which had been resuspended in 0.1M potassium phosphate buffer pH 7.0, 2 mM EDTA. Once optimized the assay indicated a thioredoxin activity of 2.9 A/-min:mg, slightly below the activity reported by Sigma of 3.0–5.0 A/min:mg.

F. Identification of TcpG. In order to further characterize the TcpG gene and to facilitate the development of immunological tools for the detection of the TcpG gene product, the sequence of the fusion gene was determined. The deduced amino acid sequence of TcpG contained a hydrophilic region as indicated by Kyte and Doolittle analysis. This region was used to generate a synthetic peptide corresponding to TcpG residues 121–144, against which the TcpG specific antibodies were raised. This antiserum was then used to identify cross reactive proteins. Whole cell protein samples were prepared from strains RT110.21 (TcpA-), 1B1 (toxR-), 0395 (wild type), and KP8-96 (TcpG-phoA) and were separated by SDS-PAGE and immunobloted using antisera directed against the synthetic TcpG peptide. A 25 kDa protein recognized by the TcpG antibodies was detected in RT110.21 and 0395 protein extracts, and to a lesser extent in 1B1. This apparent regulation by ToxR is consistent with the manner in which the TcpG gene was originally identified. The KP8-96 lane lacked the 25 kDa protein, but instead expressed a 64 kDa cross-relative fusion protein. This size correlates to the sequence data which reveals a 441 bp ORF which would make an approximate 16 kDa contribution to the fusion protein, with the alkaline phosphatase portion contributing an additional 48 kDa for 64 kDa total. This 64 kDa protein also cross-reacts with anti-alkaline phosphatase antibodies.

G. Subcellular Localization of TcpG. Since the anti-peptide antibody appeared to be specific for TcpG, it was utilized to localize the TcpG protein. If TcpG were to function as an adhesion molecule as was initially expected, it should be surfaced exposed. Repeated attempts utilizing whole cell ELSIA, immunofluorescence and immunoelection microscopy of intact bacteria failed to detect TcpG on the exterior of the bacteria. This suggested that TcpG is not surface exposed or that the native epitopes are inaccessible or unrecognized by the peptide generated antibodies. Since PhoA fusion data indicated that TcpG was an exported molecule, a fractionation technique utilizing polymyxin B sulfate was employed to localize TcpG to the periplasm, or membrane fractions. Cells were washed and then treated with polymixin B, allowing the periplasmic contents to be solubilized. Whole cells and spheroplasts were pelleted by centrifugation, thus leaving the periplasmic contents in the supernatant. Pellets and supernatants were then examined for the presence of TcpG. A Western blot of polymyxin B fractionated 0395 probed with anti-TcpG antibodies shows all of the detectable TcpG was released from the periplasm and contained in the supernatant fraction by this method. The periplasmic localization of TcpG was further supported by immunogold labeling the Lowicryl thin sections of 0395 with anti-TcpG. Label showed TcpG to be localized exclusively to the periplasm and not associated with the TCP pilus. Thus, the periplasmic localization of TcpG suggested that TcpG functions not as an adhesion molecule but indirectly by modulating TCP function, perhaps at a step during pilus assembly.

H. Purification of TcpG. Fractionation data prompted purification of TcpG from the periplasmic space in order to investigate potential activities of TcpG by in vitro assays. TcpG was purified as described hereinabove. Absorbance profiles from the G-100 elution of KP8-96 and 0395 samples were similar, with peaks consistently eluting at characteristic molecular weights. Only the amplitude of these peaks varied from run to run, these variations possibly due to slightly differing culture conditions. To compare the protein profiles of KP8-96 and 0395, samples were taken from corresponding fractions from each of the characteristic peaks. These samples were then resolved by SDS-PAGE and stained with coomassie blue. The stained protein profiles from both strains appeared to be identical, in that no additions or deletions of protein bands were apparent between the wild type and KP8-96 strains. A duplicate gel was run simultaneously and analyzed by Western blot using anti-TcpG antibodies as a probe. 0395 lanes M-Q showed a 25 kDa band recognized by anti-TcpG antibodies. Corresponding lanes in KP8-96 showed no 25 KDa reactive bands, indicating that TcpG is absent from these fractions. Interestingly, some KP8-96 fractions did contain either a 20 kDa or 29 kDa cross-relative protein. These bands have been noted previously in whole cell samples of KP8-96. The predominate cross-reactive band in strain KP8-96 is always the 64 KDa fusion, with bands of lesser intensity from 20–35 kDa, suggesting that these smaller bands are degradation products of the fusion protein since they are only seen in KP8-96 and never in 0395.

I. TcpG Thiol:disulfide interchange activity. Comparison of the predicted amino acid sequence of TcpG to entries in the Swiss protein data base using the TFASTA algorithm revealed homology to protein disulfide isomerase (PD) and several different bacterial thioredoxins. The homology centered around the reactive redox sites of thioredoxin and PDI, suggesting that a similar activity might be attributable to TcpG. The most widely used method for the monitoring of thioredoxin activity during isolation is an insulin assay that spectrophotometrically records the precipitation of the insoluble B chain that is produced when the interchain disulfides of insulin are reduced. For strains KP8-96 and 0395, G-100 elution profiles were used to choose samples from each of the characteristic elution peaks to be assayed to redox activity.

These data indicate that there are samples of 0395 which contain the 25 kDa protein detected with anti-TcpG antibodies. Those samples exhibit thiol:disulfide reactivity and adjacent control peaks show no such activity. Corresponding KP8-96 samples show no cross-relative protein and no activity. These results suggest that the "thioredoxin-like" reactive site of TcpG can function as a thiol:disulfide interchange site.

J. Altered cholera toxin subunit profile in KP8-96. Homology to thiol:sulfide interchange proteins led us to investigate whether other disulfide bond containing ToxR regulated virulence factors were affected by a mutation in TcpG. The A subunit of cholera toxin contains a disulfide bond. To assess the effects of TcpG on toxin, cultures of KP8-96 and 0395 were grown to an equivalent optical density at 600 nm under toxin expressing conditions. Both whole cell and supernatant samples were resolved by SDS-PAGE and analyzed by Western blot using a polyclonal anti-holotoxin antibodies or anti-toxin A subunit antibodies. There are several differences that are notable between the two strains. More toxin B subunit is present in the monomeric form in KP8-96 than in the wild type strain. This corresponds to a reduced pentamerization of the B subunit in the mutant strain. Most interestingly, the toxin A subunit profiles are markedly different between the two strains. The A subunit of 0395 was found in the unnicked A form in the whole cell extracts, and both the unnicked A and A1 forms in the culture supernatant. KP8-96, on the other hand, showed elevated levels of unnicked A and virtually no A1 form in the culture supernatant. Thus, the A1 form was lunable to migrate out of the bacterium due to the lack of the TcpG enzyme. The wild type 0395, however, with an intact TcpG gene sequence, was able to secrete both A and A1. This result suggests that the TcpG-PhoA fusion causes a greatly decreased ability of the A subunit to associate with the B subunit in an export competent form. A similar result is seen with a tcpG knockout mutation that does not produce a hybrid TcpG protein that could possibly interfere with the extracellular secretion process.

It has been discovered by the present inventors that a class of bacterial periplasmic proteins exists, exemplified by TcpG, that participate during the functional maturation of secreted and multimeric proteins to relieve the problem of improper protein folding. That is, TcpG may possibly have two roles in polypeptide maturation, one as a thiol oxidant similar to PDI, but also as an isomerase/chaperone where TcpG acts to locate and guide portions of polypeptide chains into a state whereby complex surfaces can form. These surfaces might otherwise be energetically unfavorable and would rarely form under physiological conditions. For example, TcpG may bind the hydrophobic carboxy terminus of TcpA during translocation preventing premature folding of the polypeptide. Once translocation is complete and the polypeptide is no longer topologically restricted, the TcpA peptide could fold while TcpG restrains the hydrophobic carboxy domain. TcpG may then act as a thiol oxidant stabilizing this conformation with a disulfide bond or as a disulfide reductant breaking disulfide bonds that have prematurely or wrongly formed in polypeptides, thus allowing the polypeptide another opportunity to refold to a functional conformation. This thiol:disulfide interchange or shuffling of disulfide bonds could continue until the functional conformation is assumed, at which point the disulfides would no longer be reactive due to thermodynamic constraints, physical inaccessibility, or both.

Thus, the present invention provides for a method for increasing the production of non-bacterial or bacterial proteins from bacteria and also provides a chain sequence for inserting into bacterial genetic material for increasing the production of non-bacterial or bacterial protein from bacteria.

Various of the features of the invention which are believed to be new are set forth in the appended claims.

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 624 base pairs
( B ) TYPE: Nucleic acid
( C ) STRANDEDNESS: Single
( D ) TOPOLOGY: Linear -continued ( i i ) MOLECULE TYPE: Genomic DNA ( i i i ) HYPOTHETICAL: No ( i v ) ANTI-SENSE: No ( v i ) ORIGINAL SOURCE:
( A ) ORGANISM: Vibrio cholerae
( B ) STRAIN: KP8-96

( x i ) SEQUENCE DESCRIPTION: SEQ ID NO: 1:

```
ATAAATCCAA TGGAGAAAGT CATGAAAAAG CTGTTTGCAC TGGTTGCAAC TCTGATGTTA   60
AGCGTGTCAG CCTATGCGGC TCAATTTAAA GAAGGTGAAC ACTACCAAGT GTTAAAAACA  120
CCCGCCTCTT CTTCACCAGT CGTCAGTGAG TTTTTCTCAT TCTACTGCCC GCACTGTAAC  180
ACTTTCGAAC CCATTATTGC TCAGTTGAAG CAGCAGTTGC CTGAAGGCGC GAAATTCCAG  240
AAAAACCACG TCTCTTTCAT GGGTGGTAAC ATGGGTCAAG CGATGAGCAA AGCGTACGCA  300
ACCATGATTG CTCTGGAAGT GGAAGATAAA ATGGTACCTG TGATGTTTAA CCGCATCCAC  360
ACTCTGCGTA AACCACCGAA AGATGAACAA GAGCTGCGCC AAATCTTCCT AGATGAAGGA  420
ATTGATGCGG CGAAATTTGA TGCGGCTTAC AACGGCTTTG CCGTGGATTC TATGGTGCGC  480
CGTTTCGATA AACAGTTCCA AGATAGCGGC CTAACCGGTG TACCTGCCGT TGTTGTTAAC  540
AACCGTTATT TGGTACAAGG TCAGTCCGTC AAATCCCTCG ACGAATATTT TGACCTAGTG  600
AACTACCTGC TGACGCTGAA GTAA                                          624
```

What is claimed is:

1. The isolated TcpG gene from *V. cholerae* which comprise the sequence SEQ ID NO:1:

```
ATAAATCCAA TGGAGAAAGT CATGAAAAAG
  CTGTTTGCAC TGGTTGCAAC TCTGATGTTA   60
AGCGTGTCAG CCTATGCGGC TCAATTTAAA
  GAAGGTGAAC ACTACCAAGT GTTAAAAACA  120
CCCGCCTCTT CTTCACCAGT CGTCAGTGAG
  TTTTTCTCAT TCTACTGCCC GCACTGTAAC  180
ACTTTCGAAC CCATTATTGC TCAGTTGAAG
  CAGCAGTTGC CTGAAGGCGC GAAATTCCAG  240
AAAAACCACG TCTCTTTCAT GGGTGGTAAC
```

-continued

```
  ATGGGTCAAG CGATGAGCAA AGCGTACGCA  300
ACCATGATTG CTCTGGAAGT GGAAGATAAA
  ATGGTACCTG TGATGTTTAA CCGCATCCAC  360
ACTCTGCGTA AACCACCGAA AGATGAACAA
  GAGCTGCGCC AAATCTTCCT AGATGAAGGA  420
ATTGATGCGG CGAAATTTGA TGCGGCTTAC
  AACGGCTTTG CCGTGGATTC TATGGTGCGC  480
CGTTTCGATA AACAGTTCCA AGATAGCGGC
  CTAACCGGTG TACCTGCCGT TGTTGTTAAC  540
AACCGTTATT TGGTACAAGG TCAGTCCGTC
  AAATCCCTCG ACGAATATTT TGACCTAGTG  600
AACTACCTGC TGACGCTGAA GTAA          624.
```

* * * * *